United States Patent [19]

Koestler

[11] Patent Number: 4,701,408

[45] Date of Patent: Oct. 20, 1987

[54] MONOCLONAL ANTIBODY TO ACTIVATED MACROPHAGES

[75] Inventor: Thomas P. Koestler, Collegeville, Pa.

[73] Assignee: SmithKline Beckman Corporation, Philadelphia, Pa.

[21] Appl. No.: 574,807

[22] Filed: Jan. 30, 1984

[51] Int. Cl.$^4$ .................. G01N 33/53; G01N 33/567; G01N 33/577
[52] U.S. Cl. .......................................... 435/7; 435/29; 435/172.2; 435/240.27; 436/548; 530/387; 935/89; 935/103; 935/110
[58] Field of Search ...................... 935/89, 95, 93, 99, 935/102, 103, 106, 110; 435/68, 172.2, 240, 241, 948, 43, 7, 29; 260/112 R, 112 B; 424/85, 86, 87; 436/548, 519, 813; 530/387, 388, 808, 809

[56] References Cited

PUBLICATIONS

Ho et al, J. of Immunology, 128, No. 3, 1221–1228, 1982.
Kohler and Milstein, Nature, vol. 256, pp. 495–497, 1975.
J. Exp. Med., 156, 1982, pp. 1286–1291.
J. Exp. Med., 154, 1981, pp. 60–76.
Journal of Immunology, 131(22), 1983, pp. 1032–1037.
Journal of Immunology, 120(6), 1978, pp. 2080–2085.

Primary Examiner—Sidney Marantz
Attorney, Agent, or Firm—Edward T. Lentz; Janice E. Williams; Alan D. Lourie

[57] ABSTRACT

A monoclonal antibody which is preferentially reactive with activated macrophages and a hybridoma which produces the antibody.

20 Claims, No Drawings

MONOCLONAL ANTIBODY TO ACTIVATED MACROPHAGES

FIELD OF THE INVENTION

This invention relates to the field of immunology and, more specifically, to the preparation and use of a monoclonal antibody to activated macrophages.

BACKGROUND INFORMATION

Macrophages are important effector cells in recognition and descruction of neoplastic cells and invasive microorganisms. Little is known about the cellular and biochemical events involved in macrophage activation. Activation is believed to involve a complex sequence of phenotypic changes that are acquired in stepwise fashion, resulting in the development of microbicidal activity followed by what appears to be the ultimate step in activation, expression of tumoricidal capacity. See, for example, Hibbs et al., *Science* 197:279-282 (1977); Meltzer, *Lymphokines* 3:319-343 (1981); and Ruco et al., *J. Immunol.* 121:2035-2042 (1978). The primary mechanism of natural activation of macrophages is believed to be through the action of the lymphokine, Macrophage Activating Factor (MAF), secreted by antigen-stimulated lymphocytes. Many agents of diverse biological origin and unrelated chemical structure including *Corynebacterium parvum*, endotoxin, muramyl dipeptide and soluble mediator(s) (lymphokines) released from antigen or mitogen-stimulated lymphocytes, have been used alone and in combination to render macrophages tumoricidal both in vitro and in vivo. See, for example, Fidler in Fundamental Mechanisms in Human Cancer Immunology, eds, Saunders et al., (Elsevier/North Holland, Amsterdam), pp. 425-438 (1981); Schultz, *Adv. Pharm. Chemotherapy* 17:157-192 (1980); and Chirigos et al., Modulation of Cellular Immunity in Cancer by Immune Modifiers (Raven Press, New York) p. 1 (1981). Whether activation by these agents occurs via a common mechanism and whether macrophages activated by different agents express qualitatively or quantitatively similar phenotypic markers such as the appearance or disappearance of cell surface antigens has not been established. Identification of immunological marker(s) whose expression parallels the activated phenotype would be of considerable value for studying the mechanism(s) of activation, for standardizing dose-response relationships between different preparations of the same activator and/or different activators and also for large scale screening for novel macrophage activating agents. It also is of potential value in diagnosis of disease states and in target-specific drug delivery.

The use of monoclonal antibodies to macrophages has been directed toward identifying cell surface antigens whose presence (or absence) correlates closely with a specific stage in monocyte-macrophage differentiation. For example, Ho et al., *J. Immunol.* 128: 1221-1228 (1982), characterized a mononuclear phagocyte antigen termed Mac-2, the expression of which is elicited only by strong inflammatory stimuli. Ezekowitz et al., *J. Exp. Med.* 154: 60-76 (1981), report that expression of a macrophage antigen recognized by another monoclonal antibody, F4/80, is significantly diminished in activated macrophages.

Taniyama et al., *J. Exp. Med.* 156:1286-1291 (1982), and Taniyama et al., *J. Immunol.* 131:1032-1037 (1983), report production of a monoclonal antibody, AcM.1, specific for pyran-activated or *Corynebacterium parvum*-activated macrophages but not thioglycollate-elicited or protease peptone-elicited macrophages. Reactivity of AcM.1 against MAF-activated macrophages was not reported.

Kaplan et al., *J. Immunol.* 120:2080 (1978), report a polyclonal antibody specific for activated macrophages.

Oldham, *J. Natl. Cancer Inst.* 70:789-796 (1983), discusses use of biological response modifiers, that is, agents which stimulate or otherwise regulate a normal biological response, in treatment of neoplasia, and screens for such modifiers.

Monoclonal antibodies were first reported by Kohler and Milstein, *Nature* 256:495-497 (1975). Since then, monoclonal antibodies have been the subject of intensive research. Interest in monoclonal antibodies stems from their ability to bind to characteristic antigens, making them useful, for example, in diagnosing disease states and delivering pharmaceutical agents to specic target cells.

SUMMARY OF THE INVENTION

One aspect of the invention is a monoclonal antibody of class IgG produced by a hybridoma formed by fusion of cells from a myeloma cell line and spleen cells previously immunized against MAF-activated macrophages, the antibody being preferentially reactive with activated macrophages.

Another aspect of the invention is the hybridoma cell line which secretes the monoclonal antibody of the invention.

Another aspect of the invention is a method of producing the antibody which comprises culturing, in vivo or in vitro, the hybridoma and recovering the antibody from the ascitic fluid or cell supernatant, respectively.

Another aspect of the invention is a method of screening a solution or mixture for macrophage activating activity comprising treating a macrophage culture with the solution or mixture for a time and under conditions sufficient to permit activation to occur, contacting the monoclonal antibody of the invention with the treated cells for a time and under conditions sufficient to permit binding of the antibody to activated cells, and assaying for enhanced binding of the antibody to the cells.

DETAILED DESCRIPTION OF THE INVENTION

The monoclonal antibody of the invention is prepared by culturing, in tissue culture (in vitro) or in ascites (in vivo), a hybridoma formed by fusion of myeloma cells and spleen cells from a mammal previously immunized against MAF-activated macrophages. As used herein, an activated macrophage is one which displays microbicidal and tumoricidal activity.

Given the instant disclosure of a hybridoma which secretes an antibody specific to a cell surface antigen which is highly expressed in activated macrophages, such hybridomas can be prepared by well known techniques. See, for example, Kohler and Milstein, *Nature* 256:495-497 (1975). In exemplifying this invention, a murine-murine hybridoma secreting an antibody raised in response to an activated mouse macrophage is disclosed. However, intra-species and other inter-species fusions can be employed. Examples of myeloma cell lines useful in hybridoma preparation are SP2/0-Ag14, X63-Ag8, NS1-Ag4/1, MPC11-45.6TG1.7, X63-Ag8.653, FO and S194/5XXXO.BU.1, all of mouse origin; 210.RCY3.Ag1.2.3 of rat origin; and U-226AR₁ and GM1500GTGAL₂, both of human origin. See, *Res. Mono. Immunol.* 3, "Monoclonal Antibodies and T-Cell Hybridomas," 1981, ed. by Hammerling et al., Elsevier/North Holland Biomedical Press, Amsterdam, page 565. Spleen cells can be obtained from any mammalian species. Similarly, the macrophages used to stimulate antibody production need not be derived from a mouse. They can be elicited from any mammal, including humans. Of critical importance, however, is that the spleen cells be immunized against MAF-activated macrophages, prior to fusion to propare the hybridoma.

Hybridomas prepared by fusing a myeloma cell line with spleen cells immunized against MAF-activated macrophages can be screened for secretion of activated macrophage-specific antibody by comparing their reactivity with activated macrophages to their reactivity with unactivated macrophages. Hybridomas having the desired property are cultured in vitro in tissue culture, or in vivo, for example, as ascites.

A lymphokine preparation containing Macrophage Activating Factor (MAF) can be prepared by known techniques. For example, MAF can be obtained from lymphocytes such as described by Fidler et al., *J. Immunol.* 117:666–673 (1976), or from a lymphoblastoid cell line such as described by McEntire et al., U.S. Pat. No. 4,405,601.

The illustrative embodiment of the hybridoma of the invention specifically described herein was prepared by fusing a mouse myeloma cell line with rat spleen cells. More particularly, it was prepared by fusion of SP2/0-Ag14 mouse myeloma cells and spleen cells from rats previously immunized against Macrophage Activating Factor (MAF)-activated mouse peritoneal macrophages, as described in Example 1, below. The hybridoma, designated 158.2, secretes monoclonal antibody MA158.2. It has been deposited in the American Type Culture Collection (ATCC), Rockville, Md., U.S.A., under accession number HB-8466 in accordance with the terms of the Budapest Treaty. Sp2/O-Ag14 is a non-secreting mouse myeloma which is resistant to 8-azaguanine (20 ug/ml) and does not survive in HAT-containing media. It has been used in preparing several monoclonal antibody producing hybridomas. See, for example, *J. Immunol.* 126:317–321 (1981).

MA158.2 is of the IgG2a subclass. It contains one heavy chain and one light chain. It does not adsorb to *Staphylococcus aureus* (Cowan 1) protein. Detectable expression of the MA158.2 reactive antigen is sensitive to cycloheximide but is unaffected by treatment of cells with protease, neuraminidase and tunicamycin.

MA158.2 does react, to varying extents, with macrophages (peritoneal exudate cells) elicted with thioglycollate, protease peptone, Concanavalin A, *Corynebacterium parvum* and bacterial membrane lipopolysaccharide (LPS). However, reactivity of MA158.2 with macrophages elicited with thioglycollate, protease peptone, Concanavalin A and LPS is significantly enhanced by a 24 hour pretreatment of the macrophages with MAF. Macrophages elicited with *C. parvum* failed to display enhanced MA158.2 antigen expression following similar treatment.

Flow cytometry was used to confirm that the enhanced antigen expression observed in MAF-treated cells was attributable to a uniform increase in antigen expression, rather than to presence of a highly reactive macrophage subpopulation. Cells in suspension were labelled with fluorescein isothiocyanate conjugated goat F(ab')₂ anti-rat Fab (Cappel Laboratories, Cochranville, Pa., U.S.A.) and analyzed on an EPICS V cell sorter (Coulter Electronics Inc., Hialeah, Fla., U.S.A.) using appropriate scatter windows to gate out cellular debris and cell aggregates and using propidium uptake to gate out dead cells. There was a significant increase (approximately 4-fold) in the mean cell fluorescence of thioglycollate-elicited, MAF-activated macrophages as compared to thioglycollate-elicited macrophages treated with a control lymphokine preparation.

MA158.2 and a series of rat monoclonal antibodies characterized in the published literature as having specificity for determinants found on mononuclear cells were examined by an indirect radioimmune binding assay (IBA) for their pattern of reactivity against thioglycollate-elicited macrophages and MAF-activated macrophages, as described in Example 1d, below. Results of these experiments are described in Table 1, which follows. Goat F(ab')₂ anti-rat Fab is designated GAR; thioglycollate-elicited macrophages are designated TPM; MAF-activated macrophages are designated AcM.

TABLE 1

Reactivity of Various Anti-Macrophage Monoclonal Antibodies with Elicited and MAF Activated Peritoneal Macrophages

| Hybridoma | Reference | Designation | Ig class | $^{125}$I-Gar bound (cpm × 10$^{-2}$) TPM | AcM |
|---|---|---|---|---|---|
| 158.2 | | MA158.2 | IgG2a | 20 ± 2 | 74 ± 2 |
| M1/70HL | (1) | MAC:1 | IgG2b | 70 ± 2 | 60 ± 1 |
| M3/38 | (2) | MAC:2 | IgG2a | 72 ± 2 | 75 ± 2 |
| M3/84 | (3) | MAC:3 | IgG1 | 20 ± 1 | 20 ± 1 |
| F4/80 | (4) | (F4/80) | IgG2b | 56 ± 2 | 36 ± 2 |
| 2.4G2 | (5) | Fc receptor | IgG1 | 46 ± 2 | 40 ± 2 |
| M1/42 | (6) | H-2K | IgG2a | 43 ± 2 | 33 ± 1 |
| M1/69HL | (6) | Heat-stable Antigen | IgG2b | 49 ± 2 | 43 ± 2 |
| M1/114 | (7) | Ia | IgG2b | 67 ± 1 | 65 ± 3 |
| M5/49 | (8) | Thy-1 | IgG2a | 6 ± 1 | 3 ± 1 |

(1) Springer et al., Eur. J. Immunol. 9:301–306 (1979).
(2) Ho et al., J. Immunol. 128:1221–1228 (1982).
(3) Ho et al., J. Biol. Chem. 258:636–642 (1983).
(4) Ezekowitz et al., J. Exp. Med. 154:60–76 (1981).
(5) Unkeless, J. Exp. Med. 150:580–596 (1979).
(6) Springer et al. (1980) in "Monoclonal Antibodies," ed. by Kennett et al., Plenum Press, New York, pp. 185–217.
(7) Bhattacharya et al., J. Immunol. 127:2488–2495 (1981).
(8) Davignon et al., J. Immunol. 127:590–595 (1981).

Expression of the MA158.2 reactive antigen was enhanced threefold following in vitro activation of thioglycollate-elicited macrophages with MAF, whereas none of the other monoclonal antibodies examined displayed any significant increase in binding concomitant with activation. In contrast to MA158.2, monoclonal antibody F4/80 displayed decreased binding to activated macrophages, consistent with previously published findings.

Several reports have described that macrophages possess trypsin sensitive Fc receptors for the IgG2a subclass. To exclude the possibility that the enhanced binding of MA158.2 is due to nonspecific binding to these Fc receptors, activated macrophages were treated with trypsin (1 mg/ml Dulbecco's modified Eagle medium) for 30 minutes at 37° C. prior to the IBA assay. Trypsin-treatment had no effect on MA158.2 binding to activated macrophages (results not shown). A lack of binding of MA158.2 to mouse neutrophils or to rat activated macrophages provided further evidence against nonspecific binding to Fc receptors (Table 2, below). Furthermore, monoclonal antibodies to Mac-2, H-2 monotypic and Thy-1 antigens, also of the rat IgG2a isotype, do not display augmented binding to MAF activated macrophages (Table 1).

Culture supernatants from the 158.2 hybridoma and M1/70, a hybridoma which secretes monoclonal antibody that binds to the iC3B receptor on murine and human granulocytes, were used to analyze the specificity of each antibody towards various lymphoid cells as detected by IBA. Dilutions of hybridoma supernatants used were in antibody excess, as previously determined employing thioglycollate-elicited, MAF-activated macrophages as targets. The specificity of MA158.2 binding was restricted to murine cells of the mononuclear phagocyte series. See, Table 2, below, in which %M means the percentage of total cells determined to be macrophages; RPM means resident peritoneal macrophages; M means macrophages; TPM and AcM are as defined for Table 1, above. This was confirmed in several experiments in which replicate cell populations, pre-treated with MAF, were analyzed for the expression of MA158.2 antigen by immunofluorescence (results not shown). Nylon wool purified splenic T-cells, blood leukocytes and suspensions of cells from lymph node and thymus failed to bind MA158.2 (results not shown).

TABLE 2

Expression of MA158.2 Reactive Antigen on Primary Cells

| Mouse cells | % MΦ | $^{125}$I-GAR bound (cpm × $10^{-2}$) MA158.2 | M1/70 HL |
|---|---|---|---|
| RPM | 80–90 | 6 ± 2 | 73 ± 3 |
| TPM | 95–98 | 20 ± 2 | 67 ± 3 |
| AcM | 95–98 | 78 ± 3 | 70 ± 2 |
| AcM (-rat) | 95–98 | 3 ± 1 | N.D. |
| Alveolar MΦ | 95–98 | 10 ± 1 | 30 ± 3 |
| Splenic MΦ | 60–70 | 9 ± 1 | N.D. |
| Neutrophil | 5–20 | 3 ± 1 | 48 ± 2 |

A panel of established murine cell lines of diverse biological origin, including the monocytic cell lines WEH1-231, P388D$_1$, RAW-264 and J774.1, all failed to bind MA158.2. The non-reactivity of MA158.2 with the monocytic cell lines may reflect the transformed nature of these cells and/or their antiquity in culture. See, Table 3, below.

TABLE 3

Mouse Cell Lines Which Fail to Bind MA158.2

| Cell Line | Cell Type | $^{125}$I-GAR bound × $10^{-2}$ MA158.2 | M1/70 |
|---|---|---|---|
| X63-Ag8 | Plasmacytoma | 2 | 2 |
| SP2/0-Ag14 | Plasmacytoma | 2 | 2 |
| YAC | Lymphoma | 2 | 2 |
| WEH1-231 | Monocytic | 3 | 40 |
| P388D$_1$ | Monocytic | 3 | 65 |
| RAW-264 | Monocytic | 3 | 64 |
| J774.1 | Monocytic | 3 | 92 |
| B16 | Melanoma | 2 | 2 |

The antigen detected by MA158.2 was not strain or sex specific and was found on thioglycollate-elicited, MAF-activated macrophages from mice carrying H-2$^d$, H-2$^b$ and H-2$^k$ haplotypes, respectively. See, Table 4, below, in which TPM and AcM are as defined for Table 1, above.

TABLE 4

Sex and Strain Specificity of MA158.2

| Mouse Strain | Haplotype | Sex | $^{125}$I-GAR bound (cpm × $10^{-2}$) TPM | AcM |
|---|---|---|---|---|
| C57BL/6 | H-2$^b$ | ♂ | 20 ± 1 | 79 ± 3 |
|  |  | ♀ | 19 ± 2 | 78 ± 1 |
| DBA/2 | H-2$^d$ | ♂ | 19 ± 2 | 72 ± 2 |
|  |  | ♀ | 19 ± 1 | 75 ± 3 |
| BALB/c | H-2$^d$ | ♂ | 20 ± 1 | 74 ± 1 |
|  |  | ♀ | 20 ± 2 | 75 ± 1 |
| C3H/HeN | H-2$^k$ | ♂ | 17 ± 1 | 71 ± 3 |
|  |  | ♀ | 16 ± 2 | 62 ± 1 |

The monoclonal antibody of the invention can be used to screen for biological response modifiers having macrophage activating activity, such as natural products or synthetic compounds. Such agents have potential utility in therapy of neoplasia as well as of microbial infection. In a typical screen, a control population of macrophages is activated with MAF as described in the Examples which follow. A second population is treated in similar fashion with a solution or mixture, such as a fermentation broth, which is being tested. Activation of the two populations is then assayed, such as by an indirect radioimmune binding assay (IBA), which comprises contacting the subpopulation with an excess of MA158.2 followed by washing and contacting the population with a labelled antibody to MA158.2, such as an anti-rat antibody. Such IBA is described in the Examples, below. Any enhancement of reactivity may be indicative of macrophage activating activity, although materials showing activity roughly equivalent to or greater than that of MAF, that is, at least about 3-fold in an IBA, would be of interest.

The usefulness of MA158.2 as a tool for distinguishing among macrophage populations elicited with different agents is illustrated by the above data showing that macrophages elicited with different agents display different quantitative levels of expression of MA158.2 reactive antigen before and after treatment with MAF. Although macrophages elicited with *C. parvum* did not display enhanced binding of MA158.2 following treatment with MAF, these macrophages express tumoricidal properties against B16 melanoma cells in the absence of MAF treatment. Furthermore, *C. parvum*-activated macrophages are significantly smaller than macrophages elicited with thioglycollate, protease peptone, Concanavalin A and LPS, which may account for the lower level of expression of MA158.2 reactive antigen. The determination of epitope density of the MA158.2 reactive antigen on macrophages elicited with different agents has thus far been unsuccessful due to a loss of binding properties of MA158.2 following iodination. In light of the well-documented heterogeneity in biochemical, morphological and, more importantly, functional characteristics, macrophages elicited by diverse agents can be viewed as distinct cell subpopulations that are capable of responding differently to activation stimuli.

EXAMPLES

Example 1

Production and characterization of MA158.2

A. Macrophage Activating Factor

A lymphokine preparation containing MAF was obtained from cell-free supernatants from cultures of normal F344 rat lymphocytes incubated for 48 hr with immobilized Conconvalin A (Pharmacia Fine Chemicals, Piscataway, N.J., U.S.A.) substantially as described by Fidler et al., *J. Immunol.* 117:666–673 (1976).

B. Macrophages

Peritoneal exudate cells (PEC) were obtained from specific pathogen-free inbred female C57BL/6 mice following intraperitoneal injection of 2.0 ml of Brewer's thioglycollate medium (Difco Laboratories, Detroit, Mich., U.S.A.). This strain is available from Charles River Inc., Portage, Mich., U.S.A. The time of elicitation was five days.

PEC were harvested by lavage with $Ca^{2+}$- $Mg^{2+}$-free Hank's balanced salt solution at room temperature (20°–25° C.). The recovered cell suspensions were centrifuged at 250×g, resuspended at a cell density of $2 \times 10^6$ PEC/ml in Dulbecco's modified Eagle medium (DMEM) and plated into plastic tissue culture dishes. To obtain an adherent population enriched with macrophages, PEC were incubated for 2 hr at 37° C. in a humidified 5% $CO:95\%$ air atmosphere. The cultures were rinsed three times with DMEM to remove nonadherent cells and treated with a solution of the Macrophage Activating Factor in DMEM, at a final dilution of 1:5. Greater than 95% of the adherent cells were shown to be macrophages by their ability to phagocytose carbon particles and by positive straining for non-specific esterase as described by Tucker et al., *J. Immunol. Methods* 14:267–269 (1977).

C. Monoclonal Antibodies

PEC elicited by thioglycollate substantially as described above were cultured for 2 hours at $10^7$ cells/100 mm tissue culture dish. Nonadherent cells were removed by washing with DMEM. The adherent monolayers were treated with a 1:5 dilution of the MAF. Following treatment for 24 hr, the MAF-activated macrophages were washed three times with DMEM and harvested with a rubber policeman. Cell viability as determined by trypan blue dye exclusion was 40 to 60%.

Lewis rats (Charles River) were primed by intraperitoneal and subcutaneous injection of $2 \times 10^7$ activated macrophages in complete Freund's adjuvant (total volume of 1 ml per rat). Two weeks later, they were inoculated in a similar fashion but with incomplete adjuvant. Five further injections of a similar number of cells were administered intraveneously over the following 15 weeks. Spleens were removed three days after the final inoculation.

The spleen cells were fused with the SP2/0-Ag14 mouse myeloma cell line (ATCC CRL-1581, Russel et al., *Nature* 253:461–463 (1979)), substantially by the standard procedure, that is, the procedure described by Kohler and Milstein, *Nature* 256:495–497 (1975), using polyethylene glycol to promote fusion and HAT to select hybridomas.

Over 1500 hybridoma clone supernatants were screened, by an indirect radioimmune binding assay (IBA), as described below, for antibody that preferentially bound to activated macrophages, as compared to binding by thioglycollate-elicited macrophages treated with a control lymphokine preparation which was devoid of MAF activity. Such control preparations were obtained from normal F344 rat lymphocyte cell-free supernatants harvested as described above but from lymphocyte cultures not exposed to Conconavalin A.

A hybridoma designated 158.2, secreting antibody MA158.2, with the appropriate specificity was cloned twice by the limiting dilution method. The cells were grown in tissue culture in DMEM with 10% fetal calf serum, or as ascites in pristane-primed, sublethally-irradiated BALB/C nude mice. (Pristane, 2,6,10,14-tetramethyl pentadecane, was purchased from Sigma Chemicals, St. Louis, Mo., U.S.A.).

D. IBA

Binding of rat monoclonal antibody to cells was detected by $^{125}I$-labelled goat F(ab')$_2$ anti-rat Fab. The goat anti-rat antibody, free of cross-reactivity with mouse immunoglobulin, was obtained from Cappel Laboratories, Cochranville, Pa., U.S.A. Trace labelling with $Na^{125}I$ was carried out by New England Nuclear, Boston, Mass., U.S.A.

Example 2

Correlation of MA158.2 binding with acquisition of tumoricidal activity

Replicate macrophage cultures were examined to correlate the kinetics of MAF-induced expression of the MA158.2-reactive antigen with development of tumoricidal activity.

Macrophage-mediated cytotoxicity was assessed in an in vitro 72 hr assay employing B16 melanoma target cells labeled for 18 hr with 5-[$^{125}I$] iodo-2'-deoxyuridine. Effector cells (thioglycollate-elicited marophages) were treated for 24 hr in vitro with a final dilution (1:5) of either MAF or supernatant from control lymphocytes. Following activation, macrophage cultures ($10^5$/well) were washed twice with DMEM containing 10% fetal calf serum (CDMEM) and radiolabelled B16 melanoma target cells ($5 \times 10^3$/well) were added in a final volume of 0.2 ml of CDMEM. Seventy-two hours after plating, the cultures were washed with CDMEM to remove non-adherent cells and the remaining cells were lysed with 0.1 ml of 0.2N NaOH. B16 melanoma target cells, without macrophages, were plated as a control to determine spontaneous release. Lysates were absorbed onto cotton swabs, placed directly into $12 \times 72$ mm tubes, and radioactivity measured in a gamma counter.

Acquisition of tumoricidal capacity following treatment with MAF paralleled increased expression of antigen recognized by MA158.2. Maximal expression of tumoricidal capacity and MA158.2 reactive antigen was essentially complete following treatment with MAF for 24 hr. Previous experiments demonstrated that maximal expression of tumoricidal properties in this assay required a 24 hr exposure to MAF.

The above disclosure, including the Examples, fully describes the invention and the preferred embodiments thereof. However, the invention comprises all modifications thereof coming within the scope of the following claims.

I claim:

1. A monoclonal antibody of class IgG produced and secreted by a hybridoma formed by fusion of cells from a myeloma cell line and spleen cells from a mammal previously immunized with MAF-activated macrophages, the antibody being reactive with thioglycollate-, proteose-peptone-, Concanavalin A-, and LPS-elicited macrophages, but which is at least about three-fold more reactive with MAF-activated macrophages than with thioglycollate-elicited macrophages.

2. The monoclonal antibody of claim 1 which has one heavy and one light chain, does not adsorb to *S. aureus* (Cowan 1) protein, is of the IgG2a subclass, and reacts with macrophages elicited with Corynebacterium parvum.

3. The monoclonal antibody of claim 2 produced and secreted by the hybridoma wherein the spleen cells are previously immunized against mouse macrophages.

4. The monoclonal antibody of claim 3 produced and secreted by the hybridoma wherein the myeloma cell line is a murine myeloma cell line and the spleen cells are from a murine animal.

5. The monoclonal antibody of claim 4 produced and secreted by the hybridoma wherein the myeloma cell line is SP2/O-Ag14.

6. The monoclonal antibody of claim 5 wherein the hybridoma is 158.2 (ATCC HB-8466).

7. The monoclonal antibody of claim 5 which is MA158.2 (monoclonal antibody from ATCC HB 8466).

8. A hybridoma comprising a cell formed by fusion of a myeloma cell line and spleen cells from a mammal previously immunized with MAF-activated macrophages which hybridoma produces and secretes a monoclonal antibody of class IgG which reacts with thioglycollate-, proteose-peptone-, Concanavalin A- and LPS-elicited macrophages, but which is at least about three-fold more reactive with MAF activated macrophages than with thioglycollate-elicited macrophages.

9. The hybridoma of claim 8 which produces and secretes an antibody which has one heavy and one light chain, does not adsorb to *S. aureus* (Cowan 1) protein, is of the IgG2a subclass, and reacts with macrophages elicited with *Corynebacterium parvum*.

10. The hybridoma of claim 9 wherein the myeloma cell line is a murine myeloma cell line and the spleen cells are from a murine animal.

11. The hybridoma of claim 10 wherein the myeloma cell line is SP2/O-Ag14.

12. The hybridoma of claim 11 which is 158.2 (ATCC HB-8466).

13. A method of screening a solution or mixture for macrophage activating activity which comprises treating a macrophage culture with the solution or mixture for a time and under conditions sufficient to permit activation to occur; contacting the treated culture with an antibody of class IgG produced and secreted by a hybridoma formed by fusion of cells from a myeloma cell line and spleen cells from a mammal previously immunized with MAF-activated macrophage, the antibody being reactive with thioglycollate-, proteose-peptone-, Conconavalin A-, and LPS-elicited macrophages, but which is at least about three-fold more reactive with MAF-activated macrophages that with thioglycollate-elicited macrophages, for a time and under conditions sufficient to permit binding of the antibody to activated cells; and assaying for enhanced binding of the antibody to the cells, said enhanced binding being an indication of the presence of macrophage activating activity.

14. The method of claim 13 wherein the antibody has one heavy and one light chain, does not adsorb to *S. aureus* (Cowan 1) protein, is of the IgG2a subclass, and reacts with macrophages elicited with *Corynebacterium parvum*.

15. The method of claim 14 wherein the spleen cells are previously immunized with mouse macrophages.

16. The method of claim 15 wherein the myeloma cell line is a murine myeloma cell line and the spleen cells are from a murine animal.

17. The method of claim 16 wherein the macrophage culture is derived from a mouse.

18. The method of claim 16 wherein the myeloma cell line is SP2/0-Ag14.

19. The method of claim 18 wherein the antibody is MA158.2 (monoclonal antibody from ATCC HB-8466).

20. The method of claim 18 wherein the macrophage culture is derived from a mouse.

* * * * *